(12) United States Patent
McKay

(10) Patent No.: US 9,107,983 B2
(45) Date of Patent: *Aug. 18, 2015

(54) OSTEOCONDUCTIVE MATRICES COMPRISING STATINS

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 549 days.

This patent is subject to a terminal disclaimer.

(21) Appl. No.: 12/913,237

(22) Filed: Oct. 27, 2010

(65) Prior Publication Data

US 2012/0107401 A1    May 3, 2012

(51) Int. Cl.
| A61L 27/44 | (2006.01) |
| A61L 27/54 | (2006.01) |
| A61K 9/00 | (2006.01) |
| A61K 35/32 | (2006.01) |

(52) U.S. Cl.
CPC ............ *A61L 27/446* (2013.01); *A61L 27/54* (2013.01); *A61L 2300/412* (2013.01); *A61L 2430/02* (2013.01)

(58) Field of Classification Search
CPC .............. A61L 27/446; A61L 2430/02; A61L 2300/412; A61L 27/54
USPC ......................................... 424/484, 549, 602
See application file for complete search history.

(56) References Cited

U.S. PATENT DOCUMENTS

| 4,645,854 A | 2/1987 | Verhoeven et al. |
| 4,863,957 A | 9/1989 | Neuenschwander et al. |
| 4,866,068 A | 9/1989 | Rooney |
| 4,894,465 A | 1/1990 | Lee et al. |
| 4,894,466 A | 1/1990 | Lee et al. |
| 4,904,646 A | 2/1990 | Karanewsky et al. |
| 4,929,437 A | 5/1990 | Tobert |
| 4,946,860 A | 8/1990 | Morris et al. |
| 5,023,250 A | 6/1991 | Adams et al. |
| 5,025,000 A | 6/1991 | Karanewsky |
| 5,091,378 A | 2/1992 | Karanewsky et al. |
| 5,202,327 A | 4/1993 | Robl |
| 5,256,692 A | 10/1993 | Gordon et al. |
| 5,366,738 A | 11/1994 | Rork et al. |
| 5,531,791 A * | 7/1996 | Wolfinbarger, Jr. ........ 623/23.63 |
| 5,620,876 A | 4/1997 | Davis et al. |
| 5,622,985 A | 4/1997 | Olukotun et al. |
| 5,763,414 A | 6/1998 | Bok et al. |
| 5,798,375 A | 8/1998 | Tsujita et al. |
| 6,355,810 B1 | 3/2002 | Griffin et al. |
| 6,376,476 B1 | 4/2002 | Gasper et al. |
| 6,403,637 B1 | 6/2002 | Partridge |
| 6,410,521 B1 | 6/2002 | Mundy et al. |
| 6,472,421 B1 | 10/2002 | Wolozin |
| 6,534,088 B2 | 3/2003 | Guivarc'h et al. |
| 6,569,461 B1 | 5/2003 | Tillyer et al. |
| 6,696,084 B2 | 2/2004 | Pace et al. |
| 6,811,786 B1 | 11/2004 | Farmer et al. |
| 6,838,436 B1 | 1/2005 | Mundy et al. |
| 7,041,309 B2 | 5/2006 | Remington et al. |
| 7,101,907 B2 | 9/2006 | Gasper et al. |
| 7,108,862 B2 | 9/2006 | Remington et al. |
| 7,288,535 B2 | 10/2007 | Garrett |
| 7,329,418 B2 | 2/2008 | Solomon et al. |
| 7,692,034 B2 | 4/2010 | Ohrlein et al. |
| 7,763,278 B2 | 7/2010 | Cooper et al. |
| 7,811,782 B2 | 10/2010 | Blackman et al. |
| 2001/0006662 A1 | 7/2001 | Krill et al. |
| 2001/0024658 A1 | 9/2001 | Chen et al. |
| 2002/0028826 A1 | 3/2002 | Robl et al. |
| 2002/0049155 A1 | 4/2002 | Hogenkamp |
| 2002/0061509 A1 | 5/2002 | Mundy et al. |
| 2002/0115695 A1 | 8/2002 | Paralkar |
| 2002/0142940 A1 | 10/2002 | Graham et al. |
| 2002/0156122 A1 | 10/2002 | Mach |
| 2003/0083231 A1 | 5/2003 | Ahlem et al. |
| 2003/0092603 A1 | 5/2003 | Mundy et al. |
| 2003/0144198 A1 | 7/2003 | Collins |
| 2003/0149010 A1 | 8/2003 | Keller et al. |
| 2003/0158081 A1 | 8/2003 | March et al. |
| 2003/0181374 A1 | 9/2003 | Mundy et al. |
| 2003/0183962 A1 | 10/2003 | Buiser et al. |
| 2003/0229015 A1 | 12/2003 | Fogelman et al. |
| 2003/0236573 A1 | 12/2003 | Evans et al. |
| 2004/0002770 A1 | 1/2004 | King et al. |

(Continued)

FOREIGN PATENT DOCUMENTS

| EP | 0306264 A2 | 3/1989 |
| EP | 0463456 A1 | 1/1992 |

(Continued)

OTHER PUBLICATIONS

Garrett IR, Gutierrez GE, Rossini G, Nyman J, McCluskey B, Flores A, Mundy GR. Locally delivered lovastatin nanoparticles enhance fracture healing in rats. J Orthop Res. Oct. 2007;25(10):1351-7. PubMed PMID: 17506505. Abstract, May 1, 2012.

Liu XM, Miller SC, Wang D. Beyond oncology—application of HIPMA copolymers in non-cancerous diseases. Adv Drug Deliv Rev. Feb. 17, 2010;62(2):258-71. Epub Nov. 10, 2009. Review. PubMed PMID: 19909776; PubMed Central PMCID: PMC2821970. Abstract.

Thylin MR, McConnell JC, Schmid MJ, Reckling RR, Ojha J, Bhattacharyya I, Marx DB, Reinhardt RA. Effects of simvastatin gels on murine calvarial bone. J Periodontol. Oct. 2002;73(10):1141-8. PubMed PMID: 12416771. Abstract.

(Continued)

*Primary Examiner* — Anoop Singh
(74) *Attorney, Agent, or Firm* — Sorell Lenna & Schmidt LLP

(57) ABSTRACT

Osteoconductive matrices and methods are provided that have one or more statins disposed therein. The matrices may be injected into a fracture site. The osteoconductive matrices provided allow for sustain release of the statin and facilitate bone formation and repair of the fracture site.

18 Claims, 2 Drawing Sheets

(56) References Cited

U.S. PATENT DOCUMENTS

| | | |
|---|---|---|
| 2004/0005306 A1 | 1/2004 | Loscalzo et al. |
| 2004/0006125 A1* | 1/2004 | Remington et al. .......... 514/423 |
| 2004/0033258 A1 | 2/2004 | Koike |
| 2004/0072894 A1 | 4/2004 | Kerc |
| 2004/0077648 A1 | 4/2004 | Timmer et al. |
| 2004/0092565 A1 | 5/2004 | Kindness et al. |
| 2004/0101557 A1 | 5/2004 | Gibson et al. |
| 2004/0132771 A1 | 7/2004 | Babcock et al. |
| 2004/0148013 A1 | 7/2004 | Epstein et al. |
| 2004/0158194 A1 | 8/2004 | Wolff et al. |
| 2004/0170663 A1 | 9/2004 | Wang et al. |
| 2004/0185102 A1 | 9/2004 | Friesen et al. |
| 2004/0197398 A1 | 10/2004 | Friesen et al. |
| 2004/0229878 A1 | 11/2004 | DiMauro et al. |
| 2004/0254238 A1 | 12/2004 | Garrett et al. |
| 2005/0004369 A1 | 1/2005 | Whitehouse et al. |
| 2005/0025765 A1 | 2/2005 | DiMauro et al. |
| 2005/0026979 A1 | 2/2005 | Ghazzi et al. |
| 2005/0038001 A1 | 2/2005 | Attawia et al. |
| 2005/0038007 A1 | 2/2005 | Curatolo et al. |
| 2005/0038102 A1 | 2/2005 | Liao et al. |
| 2005/0043364 A1 | 2/2005 | Kennedy et al. |
| 2005/0058688 A1 | 3/2005 | Boerger et al. |
| 2005/0119269 A1 | 6/2005 | Rao et al. |
| 2005/0152905 A1 | 7/2005 | Omoigui |
| 2005/0227983 A1 | 10/2005 | Timmer et al. |
| 2005/0239884 A1 | 10/2005 | Meyer et al. |
| 2005/0245905 A1 | 11/2005 | Schmidt et al. |
| 2005/0261354 A1 | 11/2005 | Griffin et al. |
| 2006/0002979 A1 | 1/2006 | Ashammakhi et al. |
| 2006/0013850 A1 | 1/2006 | Domb |
| 2006/0013851 A1 | 1/2006 | Giroux |
| 2006/0253100 A1 | 11/2006 | Burright et al. |
| 2007/0099868 A1 | 5/2007 | Harats et al. |
| 2007/0231305 A1* | 10/2007 | Noll et al. .................... 424/93.7 |
| 2007/0259019 A1 | 11/2007 | McKay |
| 2007/0264348 A1 | 11/2007 | Ryde et al. |
| 2008/0038316 A1 | 2/2008 | Wong et al. |
| 2008/0114465 A1 | 5/2008 | Zanella et al. |
| 2008/0147197 A1 | 6/2008 | McKay |
| 2008/0152691 A1* | 6/2008 | Drapeau et al. ............. 424/426 |
| 2008/0206831 A1* | 8/2008 | Coffey et al. ................ 435/176 |
| 2008/0213378 A1 | 9/2008 | Cooper et al. |
| 2009/0142385 A1 | 6/2009 | Gross et al. |
| 2009/0148496 A1 | 6/2009 | Schmitz et al. |
| 2009/0157193 A1* | 6/2009 | McKay ..................... 623/23.72 |
| 2009/0181098 A1 | 7/2009 | Garrett et al. |
| 2009/0196910 A1 | 8/2009 | Yie et al. |
| 2009/0196920 A1 | 8/2009 | Carminati et al. |
| 2009/0246244 A1* | 10/2009 | McKay et al. ............... 424/423 |
| 2009/0258049 A1 | 10/2009 | Klein et al. |
| 2009/0297573 A1 | 12/2009 | Sur et al. |
| 2010/0015229 A1 | 1/2010 | Duncalf et al. |
| 2010/0228097 A1 | 9/2010 | McKay |

FOREIGN PATENT DOCUMENTS

| | | |
|---|---|---|
| EP | 0807435 A2 | 11/1997 |
| EP | 1029928 B1 | 7/2010 |
| JP | 0320226 A | 1/1991 |
| WO | 9317991 A1 | 9/1993 |
| WO | 9963994 A1 | 12/1999 |
| WO | 0018396 A1 | 4/2000 |
| WO | 03094923 A1 | 11/2003 |
| WO | 2004024165 A1 | 3/2004 |
| WO | 2004064865 A1 | 8/2004 |
| WO | 2005007209 A1 | 1/2005 |
| WO | 2005079790 A1 | 9/2005 |
| WO | 2005099760 A1 | 10/2005 |
| WO | 2006119598 A2 | 11/2006 |
| WO | 2008014066 A1 | 1/2008 |
| WO | 2010014184 A1 | 2/2010 |

OTHER PUBLICATIONS

Whang K, Mcdonald J, Khan A, Satsangi N. A novel osteotropic biomaterial OG-PLG: Synthesis and in vitro release. J Biomed Mater Res A. Aug. 1, 2005;74(2):237-46. PubMed PMID: 15981201. Abstract.

International Search Report and Written Opinion for PCT/US2011/056512, the counterpart application, mailed on May 30, 2012.

* cited by examiner

OSTEOCONDUCTIVE MATRICES COMPRISING STATINS

BACKGROUND

Bone is a composite material that is composed of impure hydroxyapatite, collagen and a variety of non-collagenous proteins, as well as embedded and adherent cells. Due to disease, a congenital defect or an accident, a person may lose or be missing part or all of one or more bones or regions of cartilage in his or her body, and/or have improper growth or formation of bone and/or cartilage.

Mammalian bone tissue is known to contain one or more proteinaceous materials that are active during growth and natural bone healing. These materials can induce a developmental cascade of cellular events that result in bone formation. Typically, the developmental cascade of bone formation involves chemotaxis of mesenchymal cells, proliferation of progenitor cells, differentiation of cartilage, vascular invasion, bone formation, remodeling and marrow differentiation.

When bone is damaged, often bone grafting procedures are performed to repair the damaged bone especially in cases where the damage is complex, poses a significant risk to the patient, and/or fails to heal properly. Bone grafting is also used to help fusion between vertebrae, correct deformities, or provide structural support for fractures of the spine. In addition to fracture repair, bone grafting is also used to repair defects in bone caused by birth defects, traumatic injury, or surgery for bone cancer.

There are at least three ways in which a bone graft can help repair a defect. The first is called osteogenesis, the formation of new bone within the graft. The second is osteoinduction, a process in which molecules contained within the graft (e.g., bone morphogenic proteins) convert the patient's cells into cells that are capable of forming bone. The third is osteoconduction, a physical effect by which a matrix often containing graft material acts as a scaffold on which bone and cells in the recipient are able to form new bone.

The source of bone for grafting can be obtained from bones in the patient's own body (e.g., hip, skull, ribs, etc.), called autograft, or from bone taken from other people that is frozen and stored in tissue banks, called allograft. The source of bone may also be derived from animals of a different species called a xenograft.

Some grafting procedures utilize a variety of natural and synthetic matrices with or instead of bone (e.g., collagen, silicone, acrylics, hydroxyapatite, calcium sulfate, ceramics, etc.). To place the matrix at the bone defect, the surgeon makes an incision in the skin over the bone defect and shapes the matrix to fit into the defect.

Often times, depending on the anatomic site for implantation, substantially spherical or rounded particles such as for example, bone particles, calcium phosphate ceramics, etc. are added to the matrix so that it can withstand certain loads that can be placed on it. They also enhance osseointegration of the matrix. While these particles added to the matrices provide some compression resistance, they often do not provide compression resistance in high load bearing areas such as for example in the spine. Therefore, as a result of excessive compression, the matrix may fail to integrate properly into the bone defect site or may be dislodge from the bone defect site to a blood vessel and cause an ischemic event (e.g., embolism, necrosis, edema, infarction, etc.), which could be detrimental to the patient.

As persons of ordinary skill are aware, growth factors (e.g., bone morphogenic protein-2) may be placed on the matrix in order to spur the patient's body to begin the formation of new bone and/or cartilage. These growth factors act much like a catalyst, encouraging the necessary cells (including, but not limited to, mesenchymal stem cells, osteoblasts, and osteoclasts) to more rapidly migrate into the matrix, which is eventually resorbed via a cell-mediated process and newly formed bone is deposited at or near the bone defect. In this manner severe fractures may be healed, and vertebrae successfully fused. Unfortunately, many growth factors tend to be very expensive and increase the cost of bone repair.

One class of molecules known to the medical profession are statins. Statins are a family of molecules sharing the capacity to competitively inhibit the hepatic enzyme 3-hydroxy-3-methylglutaryl coenzyme A (HMG-CoA) reductase. This enzyme catalyses the rate-limiting step in the L-mevalonate pathway for cholesterol synthesis. Oral statin use blocks cholesterol synthesis and is effective in treating hypercholesterolemia. In recent years, oral statins have been shown to reduce cardiovascular-related morbidity and mortality in patients with and without coronary disease.

To date, locally delivered matrices containing statins have not been appreciated as providing a stable microenvironment that facilitates bone growth, particularly when used in bone defects, fractures and/or voids. Thus, there is a need to develop new matrices that improve repair of bone defect, voids and/or fractures.

SUMMARY

In some embodiments, implantable matrices and methods are provided that retain the statin at or near the bone defect (e.g., fracture, void, etc.) to facilitate healing of the bone defect and avoid adverse local tissue reactions to the statin. In some embodiments, the implantable matrices provided are cohesive and osteoconductive and allow gaps and fractures to be filled with new bridging bone faster. All of which leads to a reduced time for healing. In some embodiments, the implantable matrices and methods provided are easy and less costly to manufacture because the active ingredient is a small molecule statin, as opposed to a larger, and, sometimes, more expensive and less stable growth factor.

In one embodiment, the implantable matrices and methods allow easy delivery to the target tissue site (e.g., fracture site, synovial joint, at or near the spinal column, etc.) using a flowable matrix that hardens upon contact with the target tissue. In this way, accurate and precise implantation of the matrix in a minimally invasive procedure can be accomplished.

In a second embodiment, there is an implantable osteoconductive matrix configured to fit at or near a target tissue site, the matrix being malleable and cohesive and comprising a biodegradable polymer and a therapeutically effective amount of a statin disposed throughout the matrix, wherein the matrix allows influx of at least progenitor, and/or bone cells therein.

In a third embodiment, there is an implantable osteoconductive matrix configured to fit at or near a target tissue site, the matrix being injectable, malleable and cohesive and comprising calcium phosphate and a biodegradable polymer comprising collagen and a therapeutically effective amount of a statin disposed throughout the matrix, wherein the matrix allows influx of at least progenitor, and/or bone cells therein.

In a fourth embodiment, there is a method of treating a bone defect in which the bone defect site possesses at least one cavity, the method comprising inserting an implantable osteoconductive matrix configured to fit at the bone defect site, the matrix being malleable and cohesive and comprising a biodegradable polymer and a therapeutically effective amount of a statin disposed throughout the matrix, wherein the matrix allows influx of at least progenitor, and/or bone cells therein.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings where:

Figure 1:
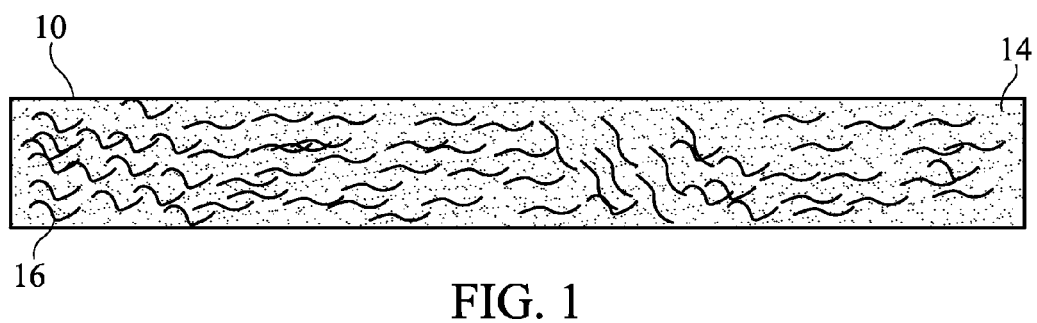
FIG. 1 illustrates a magnified side sectional view of an embodiment of the implantable matrix injected as a long strand shown with fibers embedded randomly throughout it.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations; the numerical values are as precise as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Additionally, unless defined otherwise or apparent from context, all technical and scientific terms used herein have the same meanings as commonly understood by one of ordinary skill in the art to which this invention belongs.

Unless explicitly stated or apparent from context, the following terms or phrases have the definitions provided below:

DEFINITIONS

It is noted that, as used in this specification and the appended claims, the singular forms "a," "an," and "the," include plural referents unless expressly and unequivocally limited to one referent. Thus, for example, reference to "a matrix" includes one, two, three or more matrices.

The term "biodegradable" includes that all or parts of the matrix will degrade over time by the action of enzymes, by hydrolytic action and/or by other similar mechanisms in the human body. In various embodiments, "biodegradable" includes that a matrix (e.g., sponge, sheet, etc.) can break down or degrade within the body to non-toxic components after or while a therapeutic agent has been or is being released. By "bioerodible" it is meant that the matrix will erode or degrade over time due, at least in part, to contact with substances found in the surrounding tissue, fluids or by cellular action. By "bioabsorbable" or "bioresorbable" it is meant that the matrix will be broken down and absorbed within the human body, for example, by a cell or tissue. "Biocompatible" means that the matrix will not cause substantial tissue irritation or necrosis at the target tissue site.

The term "mammal" refers to organisms from the taxonomy class "mammalian," including but not limited to humans, other primates such as chimpanzees, apes, orangutans and monkeys, rats, mice, cats, dogs, cows, horses, etc.

The term "resorbable" includes biologic elimination of the products of degradation by metabolism and/or excretion over time, for example, usually months.

The term "particle" refers to pieces of a substance of all shapes, sizes, thickness and configuration such as fibers, threads, narrow strips, thin sheets, clips, shards, etc., that possess regular, irregular or random geometries. It should be understood that some variation in dimension will occur in the production of the particles and particles demonstrating such variability in dimensions are within the scope of the present application.

The term "target tissue site" is intended to mean the location of the tissue to be treated. Typically the placement site of the matrix will be the same as the target site to provide for optimal targeted drug delivery. However, the present application also contemplates positioning the matrix at a placement site at or near the target site such that the therapeutic agent (e.g., statin) can be delivered to the surrounding vasculature, which carries the agent to the desired nearby target site. As used herein, the term "at or near" includes embodiments where the placement site and target site are within close proximity (e.g., within about 1 mm to 5 cm).

The term "autograft" as utilized herein refers to tissue intended for implantation that is extracted from the intended recipient of the implant.

The term "allograft" as utilized herein refers to tissue intended for implantation that is taken from a different member of the same species as the intended recipient.

The term "xenogenic" as utilized herein refers to material intended for implantation obtained from a donor source of a different species than the intended recipient. For example, when the implant is intended for use in an animal such as a horse (equine), xenogenic tissue of, e.g., bovine, porcine, caprine, etc., origin may be suitable.

The term "transgenic" as utilized herein refers to tissue intended for implantation that is obtained from an organism that has been genetically modified to contain within its genome certain genetic sequences obtained from the genome of a different species. The different species is usually the same species as the intended implant recipient but such limitation is merely included by way of example and is not intended to limit the disclosure here in anyway whatsoever.

The expressions "whole bone" and "substantially fully mineralized bone" refer to bone containing its full or substantially full, original mineral content that can be used. This type of bone can be used to make the matrix.

The expression "demineralized bone" includes bone that has been partially, fully, segmentally or superficially (surface) demineralized. This type of bone can be used to make the matrix.

The expression "substantially fully demineralized bone" as utilized herein refers to bone containing less than about 8% of its original mineral context. This type of bone can be used to make the matrix.

A "therapeutically effective amount" or "effective amount" is such that when administered, the drug (e.g., statin) results in alteration of the biological activity, such as, for example, promotion of bone, cartilage and/or other tissue (e.g., vascular tissue) growth, inhibition of inflammation, reduction or alleviation of pain, improvement in the condition through inhibition of an immunologic response, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments the implantable matrix is designed for sustained release. In some embodiments, the implantable matrix comprises an effective amount of a statin.

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug.

The phrases "prolonged release", "sustained release" or "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the matrix and/or component thereof, or as the result of metabolic transformation or dissolution of the therapeutic agent(s) or conjugates of therapeutic agent(s). The release need not be linear and can be pulse type dosing.

The "matrix" of the present application is utilized as a scaffold for bone and/or cartilage repair, regeneration, and/or augmentation. Typically, the matrix provides a 3-D matrix of interconnecting pores, which acts as a scaffold for cell migration. The morphology of the matrix guides cell migration and cells are able to migrate into or over the matrix, respectively. The cells then are able to proliferate and synthesize new tissue and form bone and/or cartilage. In some embodiments, the matrix is resorbable.

In some embodiments, the matrix can be malleable, cohesive, followable and/or can be shaped into any shape. The term "malleable" includes that the matrix is capable of being permanently converted from a first shape to a second shape by the application of pressure.

The term "cohesive" as used herein means that the putty tends to remain a singular, connected mass upon movement, including the exhibition of the ability to elongate substantially without breaking upon stretching.

The term "flowable" refers to a characteristic of a material whereby, after it is hydrated, it can be passed through a conduit, such as a cannula or needle, by exerting a hydraulic pressure in the conduit.

The term "injectable" includes that the material can be placed at the target tissue site by extrusion of such material from the end of a cannula, needle, tube, orifice, or the like.

The term "shape-retaining" includes that the matrix (e.g., putty, flowable material, paste, etc.) is highly viscous and unless acted upon with pressure tends to remain in the shape in which it is placed.

The term "shaped" includes that the matrix can be molded by hand or machine or injected in the target tissue site (e.g., bone defect, fracture, or void) in to a wide variety of configurations. In some embodiments, the matrix can be formed into sheets, blocks, rings, struts, plates, disks, cones, pins, screws, tubes, teeth, bones, portion of bone, wedges, cylinders, threaded cylinders, or the like, as well as more complex geometric configurations.

The term "compression" refers to a reduction in size or an increase in density when a force is applied to the matrix.

The terms "treating" and "treatment" when used in connection with a disease or condition refer to executing a protocol that may include a repair procedure (e.g., closed fracture repair procedure), administering one or more matrices to a patient (human or other mammal), in an effort to alleviate signs or symptoms of the disease or condition or immunological response. Alleviation can occur prior to signs or symptoms of the disease or condition appearing, as well as after their appearance. Thus, treating or treatment includes preventing or prevention of disease or undesirable condition. In addition, treating, treatment, preventing or prevention do not require complete alleviation of signs or symptoms, does not require a cure, and specifically includes protocols that have only a marginal effect on the patient.

The matrix may be osteogenic. The term "osteogenic" as used herein includes the ability of the matrix to enhance or accelerate the growth of new bone tissue by one or more mechanisms such as osteogenesis, osteoconduction and or osteoinduction.

The matrix may be osteoinductive. The term "osteoinductive" as used herein includes the ability of a substance to recruit cells from the host that have the potential for forming new bone and repairing bone tissue. Most osteoinductive materials can stimulate the formation of ectopic bone in soft tissue.

In some embodiments, the matrix is osteoconductive and can be delivered to other surgical sites, particularly sites at which bone growth is desired. These include, for instance, the repair of spine (e.g., vertebrae fusion) cranial defects, iliac crest back-filling, acetabular defects, in the repair of tibial plateau, long bone defects, spinal site defects or the like. Such methods can be used to treat major or minor defects in these or other bones caused by trauma (including open and closed fractures), disease, or congenital defects, for example. The term "osteoconductive" as utilized herein includes the ability of a non-osteoinductive substance to serve as a suitable template or substrate along which bone may grow. The matrix may be configured for the repair of a simple fracture, compound fracture or non-union; as an external fixation device or internal fixation device; for joint reconstruction, arthrodesis, arthroplasty or cup arthroplasty of the hip; for femoral or humeral head replacement; for femoral head surface replacement or total joint replacement; for repair of the vertebral column, spinal fusion or internal vertebral fixation; for tumor surgery; for deficit filling; for discectomy; for laminectomy; for excision of spinal cord tumors; for an anterior cervical or thoracic operation; for the repairs of a spinal injury; for scoliosis, for lordosis or kyphosis treatment; for intermaxillary fixation of a fracture; for mentoplasty; for temporomandibular joint replacement; for alveolar ridge augmentation and reconstruction; as an inlay osteoimplant; for implant placement and revision; for sinus lift; for a cosmetic procedure; and, for the repair or replacement of the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal bones or metatarsal bones The matrix may be implantable. The term "implantable" as utilized herein refers to a biocompatible device retaining potential for successful placement within a mammal. The expression "implantable device" and expressions of like import as utilized herein refers to any object implantable through surgery, injection, or other suitable means whose primary function is achieved either through its physical presence or mechanical properties.

The term "carrier" includes a diluent, adjuvant, buffer, excipient, or vehicle with which a composition can be administered. Carriers can include sterile liquids, such as, for example, water and oils, including oils of petroleum, animal, vegetable or synthetic origin, such as, for example, peanut oil, soybean oil, mineral oil, sesame oil, or the like. The statin may include a carrier.

The term "excipient" includes a non-therapeutic agent added to a pharmaceutical composition to provide a desired consistency or stabilizing effect. Excipients for parenteral formulations, include, for example, oils (e.g., canola, cottonseed, peanut, safflower, sesame, soybean), fatty acids and salts and esters thereof (e.g., oleic acid, stearic acid, palmitic acid), alcohols (e.g., ethanol, benzyl alcohol), polyalcohols (e.g., glycerol, propylene glycols and polyethylene glycols, e.g., PEG 3350), polysorbates (e.g., polysorbate 20, polysorbate 80), gelatin, albumin (e.g., human serum albumin), salts (e.g., sodium chloride), succinic acid and salts thereof (e.g., sodium succinate), amino acids and salts thereof (e.g., alanine, histidine, glycine, arginine, lysine), acetic acid or a salt or ester thereof (e.g., sodium acetate, ammonium acetate), citric acid and salts thereof (e.g., sodium citrate), benzoic acid and salts thereof, phosphoric acid and salts thereof (e.g., monobasic sodium phosphate, dibasic sodium phosphate), lactic acid and salts thereof, polylactic acid, glutamic acid and salts thereof (e.g., sodium glutamate), calcium and salts thereof (e.g., $CaCl_2$, calcium acetate), phenol, sugars (e.g., glucose, sucrose, lactose, maltose, trehalose), erythritol, arabitol, isomalt, lactitol, maltitol, mannitol, sorbitol, xylitol, nonionic surfactants (e.g., TWEEN 20, TWEEN 80), ionic surfactants (e.g., sodium dodecyl sulfate), chlorobutanol, DMSO, sodium hydroxide, glycerin, m-cresol, imidazole, protamine, zinc and salts thereof (e.g., zinc sulfate), thimerosal, methylparaben, propylparaben, carboxymethylcellulose, chlorobutanol, or heparin. The statin may include an excipient.

The term "lyophilized" or "freeze-dried" includes a state of a substance that has been subjected to a drying procedure such as lyophilization, where at least 50% of moisture has been removed. The matrix and/or statin may be lyophilized or freeze-dried.

A "preservative" includes a bacteriostatic, bacteriocidal, fungistatic or fungicidal compound that is generally added to formulations to retard or eliminate growth of bacteria or other contaminating microorganisms in the formulations. Preservatives include, for example, benzyl alcohol, phenol, benzalkonium chloride, m-cresol, thimerosol, chlorobutanol, methylparaben, propylparaben and the like. Other examples of pharmaceutically acceptable preservatives can be found in the USP. The statin and/or matrix may have preservatives or be preservative free.

Reference will now be made in detail to certain embodiments of the invention. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

In some embodiments, implantable matrices and methods are provided that retain the statin at or near the bone defect (e.g., fracture, void, etc.) to facilitate healing of the bone defect and avoid localized soft tissue adverse reactions to the statin. In some embodiments, the implantable matrices provided are cohesive and osteoconductive and allow gaps and fractures to be filled with new bridging bone faster. All of which leads to a reduced time for healing. In some embodiments, the implantable matrices and methods provided are easy and less costly to manufacture because the active ingredient is a small molecule statin, as opposed to a larger, and, sometimes, more expensive and less stable growth factor.

In one embodiment, the implantable matrices and methods allow easy delivery to the target tissue site (e.g., synovial joint, at or near the spinal column, etc.) using a flowable matrix that hardens upon contact with the target tissue. In this way, accurate and precise implantation of the matrix in a minimally invasive procedure can be accomplished.

The headings below are not meant to limit the disclosure in any way; embodiments under any one heading may be used in conjunction with embodiments under any other heading.

Matrix

The matrix provides a tissue scaffold for the cells to guide the process of tissue formation in vivo in three dimensions. The morphology of the matrix guides cell migration and cells are able to migrate into or over the matrix. The cells then are able to proliferate and synthesize new tissue and form bone and/or cartilage. In some embodiments, one or more tissue matrices are stacked on one another.

The matrix is porous and configured to allow influx of at least bone and/or cartilage cells therein. By porous is meant that the matrix has a plurality of pores. The pores of the matrix are a size large enough to allow influx of blood, other bodily fluid, and progenitor and/or bone and/or cartilage cells into the interior to guide the process of tissue formation in vivo in three dimensions.

In some embodiments, the matrix comprises a plurality of pores. In some embodiments, at least 10% of the pores are between about 50 micrometers and about 500 micrometers at their widest points. In some embodiments, at least 20% of the pores are between about 50 micrometers and about 250 micrometers at their widest points. In some embodiments, at least 30% of the pores are between about 50 micrometers and about 150 micrometers at their widest points. In some embodiments, at least 50% of the pores are between about 10 micrometers and about 500 micrometers at their widest points. In some embodiments, at least 90% of the pores are between about 50 micrometers and about 250 micrometers at their widest points. In some embodiments, at least 95% of the pores are between about 50 micrometers and about 150 micrometers at their widest points. In some embodiments, 100% of the pores are between about 10 micrometers and about 500 micrometers at their widest points.

In some embodiments, the matrix has a porosity of at least about 30%, at least about 50%, at least about 60%, at least about 70%, at least about 90% or at least about 95%, or at least about 99%. The pores may support ingrowth of cells, formation or remodeling of bone, cartilage and/or vascular tissue.

The matrix is also configured to retain a statin that has anabolic activity and stimulates bone morphogenic protein expression and bone growth into the matrix to heal bone. In some embodiments, the matrix allows for sustained release of the statin over 2 weeks to 6 months.

In some embodiments, the matrix does not contain any growth factor. In some embodiments, the matrix does contain one or more growth factors.

In some embodiments, the porous interior can hold the statin within the matrix and because the interior is porous, the statin is evenly distributed throughout the matrix when the statin is injected, soaked, contacted, or lyophilized into the matrix.

In some embodiments, a statin will be held within the interior of the matrix and released into the environment surrounding the matrix (e.g., bone defect, osteochondral defect, etc.) as the matrix degrades over time.

In some embodiments, the matrix comprises biodegradable polymeric and non-polymeric material. For example, the matrix may comprises one or more poly(alpha-hydroxy acids), poly(lactide-co-glycolide) (PLGA), polylactide (PLA), poly(L-lactide), polyglycolide (PG), polyglycolic acid (PGA), polyethylene glycol (PEG) conjugates of poly (alpha-hydroxy acids), polyorthoesters (POE), polyaspirins, polyphosphagenes, collagen, hydrolyzed collagen, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, POE, SAIB (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, polyetheretherketone, polymethylmethacrylate, silicone, hyaluronic acid, tyrosine polycarbonate, chitosan, or combinations thereof.

In some embodiments, the matrix (e.g., exterior and/or interior) comprises collagen. Exemplary collagens include human or non-human (bovine, ovine, and/or porcine), as well as recombinant collagen or combinations thereof. Examples of suitable collagen include, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XXI, human collagen type XXII, human collagen type XXIII, human collagen type XXIV, human collagen type XXV, human collagen type XXVI, human collagen type XXVII, and human collagen type XXVIII, or combinations thereof. Collagen further may comprise hetero- and homo-trimers of any of the above-recited collagen types. In some embodiments, the collagen comprises hetero- or homo-trimers of human collagen type I, human collagen type II, human collagen type III, or combinations thereof.

In some embodiments, the matrix comprises collagen-containing biomaterials from the implant market which, when placed in a bone defect, provide scaffolding around which the patient's new bone and/or cartilage will grow, gradually replacing the carrier matrix as the target site heals. Examples of suitable carrier matrices may include, but are not limited to, the MasterGraft® Matrix produced by Medtronic Sofamor Danek, Inc., Memphis, Tenn.; MasterGraft® Putty produced by Medtronic Sofamor Danek, Inc., Memphis, Tenn.; Absorbable Collagen Sponge ("ACS") produced by Integra LifeSciences Corporation, Plainsboro, N.J.; bovine skin collagen fibers coated with hydroxyapatite, e.g. Healos®, marketed by Johnson & Johnson, USA; collagen sponges, e.g. Hemostagene® marketed by Coletica S A, France, or e.g. Helisat® marketed by Integra Life Sciences Inc., USA; Collagraft® Bone Graft Matrix produced by Zimmer Holdings, Inc., Warsaw, Ind., Osteofil® (Medtronic Sofamor Danek, Inc., Memphis, Tenn.), Allomatrix® (Wright), Grafton® (Osteotech), DBX® (MTF/Synthes), Bioset® (Regeneration Technologies), matrices consisting of mineral phases such as Vitoss® (Orthivista), Osteoset® (Wright) or mixed matrices such as CopiOs® (Zimmer), or Sunnmax Collagen Bone Graft Matrix (Sunmax).

In one embodiment, the matrix can be packaged as a product including a container body holding an unhydrated matrix to be hydrated, and a removable seal operable to prevent passage of moisture into contact with the medical material. Exemplary materials to be hydrated include MasterGraft® Matrix and a MasterGraft® Putty. Exemplary hydrating fluids include blood, bone marrow, saline, water, or other fluid. The hydrating fluid may contain the statin and be used to soak the statin in the matrix.

For example, the statin can be applied to MasterGraft® Matrix or MasterGraft® Putty, which comprises type I bovine collagen and a calcium phosphate mineral phase composed of 15% hydroxyapatite and 85% beta-tricalcium phosphate. The matrix can be hydrated just prior to use so that, in some embodiments, it becomes a flowable material. Such a material can be injected through a cannula or other conduit into an in vivo location.

In some embodiments, the matrix is compression resistant where the matrix resists reduction in size or an increase in density when a force is applied as compared to matrices that are not compression resistant. In various embodiments, the matrix resists compression by at least 10%, 15%, 20%, 25%, 30%, 35%, 40%, 45%, 50%, 55%, 60%, 65%, 70%, 75%, 80%, 85%, 90%, 95%, or more in one or all directions when a force is applied to the matrix.

In one exemplary embodiment, the implantable matrix comprises a gel containing the statin that will retain the statin at the target tissue site, as the gel adheres to it. In various embodiments, the gel includes a substance having a gelatinous, jelly-like, or colloidal properties at room temperature.

The gel, in some embodiments, has the statin throughout it. Alternatively, the concentration of the statin may vary throughout it. The gel is porous and allows influx of cells to grow bone at or near the bone defect site.

In various embodiments, the gel is a hardening gel, where after the gel is applied to the target site, it hardens and allows it to conform to irregularities, crevices, cracks, and/or voids in the tissue site. For example, in various embodiments, the gel may be used to fill one or more voids in an osteolytic lesion.

In various embodiments, the gel is flowable and can be injected, sprayed, instilled, and/or dispensed to, on or in the target tissue site. In various embodiments, the gel has a pre-dosed viscosity in the range of about 1 to about 500 centipoise (cps), 1 to about 200 cps, or 1 to about 100 cps. After the gel is administered to the target site, the viscosity of the gel will increase and the gel will have a modulus of elasticity (Young's modulus) in the range of about $1\times10^4$ to about $6\times10^5$ dynes/cm$^2$, or $2\times10^4$ to about $5\times10^5$ dynes/cm$^2$, or $5\times10^4$ to about $5\times10^5$ dynes/cm$^2$.

In various embodiments, a gel is provided that hardens or stiffens after delivery. Typically, hardening gel formulations may have a pre-dosed modulus of elasticity in the range of about $1\times10^4$ to about $3\times10^5$ dynes/cm$^2$, or $2\times10^4$ to about $2\times10^5$ dynes/cm$^2$, or $5\times10^4$ to about $1\times10^5$ dynes/cm$^2$. The post-dosed hardening gels (after delivery) may have a rubbery consistency and have a modulus of elasticity in the range of about $1\times10^4$ to about $2\times10^6$ dynes/cm$^2$, or $1\times10^5$ to about $7\times10^5$ dynes/cm$^2$, or $2\times10^5$ to about $5\times10^5$ dynes/cm$^2$.

In some embodiments, the present application includes an implantable osteoconductive matrix that is in the form of a medical putty, and includes methods and materials that are useful for preparing such an osteoconductive medical putty. Preferred medical putties possess a combination of advantageous properties including a mineral content, malleability, cohesiveness, and shape retention. For example, when the matrix is implanted into a target tissue site (e.g., bone defect, void, fracture, etc.), the matrix will stay together at the target tissue site. In the context of putties containing insoluble collagen fibers, upon stretching, the advantageous putties exhibit elongation, during which the existence of substantial levels of intermeshed collagen fibers clinging to one another becomes apparent.

As used herein, the term "shape-retaining" includes that the matrix (e.g., putty, flowable material, paste, etc.) is highly viscous and unless acted upon with pressure tends to remain in the shape in which it is placed. The pressure can be by hand, machine, or from the delivery device (injection from a syringe). In some embodiments, the shape retaining feature of the matrix can be contrasted to thinner liquid matrices or liquid paste forms, which readily flow, and thus would pool or puddle upon application to a surface.

In certain features of the current application, novel combination of ingredients provide a medical putty material that not only contains a significant, high level of large particulate mineral particles, but also exhibits superior properties with respect to malleability, cohesiveness, and shape retention.

In some embodiments, the matrix of the present application will include a combination of soluble collagen and insoluble collagen. In some embodiments, the matrix does not include any soluble collagen. "Soluble collagen" refers to the solubility of individual tropocollagen molecules in acidic aqueous environments. Tropocollagen may be considered the monomeric unit of collagen fibers and its triple helix structure is well recognized. "Insoluble collagen" as used herein refers to collagen that cannot be dissolved in an aqueous alkaline or in any inorganic salt solution without chemical modification, and includes for example hides, splits and other mammalian or reptilian coverings. For example, "natural insoluble collagen" can be derived from the corium, which is the intermediate layer of an animal hide (e.g. bovine, porcine, etc.) that is situated between the grain and the flesh sides. "Reconstituted collagen" is essentially collagen fiber segments that have been depolymerized into individual triple helical molecules, then exposed to solution and then reassembled into fibril-like forms.

The matrix that is in the form of a putty contains insoluble collagen fibers. In some embodiments, the matrix comprises no soluble collagen fibers. In some embodiments, the matrix comprises both soluble and insoluble collagen fibers.

The soluble collagen and insoluble collagen fibers can first be prepared separately, and then combined. Both the soluble collagen and the insoluble collagen fibers can be derived from bovine hides, but can also be prepared from other collagen sources (e.g. bovine tendon, porcine tissues, recombinant DNA techniques, fermentation, etc.).

In certain embodiments, the putty comprises insoluble collagen fibers at a level of 0.04 g/cc to 0.1 g/cc of the putty, and soluble collagen at a level of 0.01 g/cc to 0.08 g/cc of the putty. In other embodiments, the putty includes insoluble collagen fibers at a level of about 0.05 to 0.08 g/cc in the putty, and soluble collagen at a level of about 0.02 to about 0.05 g/cc in the putty. In general, putties may include insoluble collagen fibers in an amount (percent by weight) that is at least equal to or greater than the amount of soluble collagen, to contribute beneficially to the desired handling and implant properties of the putty material. In advantageous embodiments, when the putty contains collagen, the insoluble collagen fibers and soluble collagen can be present in a weight ratio of 4:1 to 1:1, more advantageously about 75:25 to about 60:40. Further still, additional desired putties include the insoluble collagen fibers and soluble collagen in a weight ratio of about 75:25 to about 65:35, and in one specific embodiment about 70:30. The insoluble collagen fibers, in some embodiments, will be in the composition more than the soluble collagen fibers.

In some embodiments, the implantable osteoconductive matrix is a putty comprising ceramic and collagen and the ceramic has a density of about 0.15 g/cc to about 0.45 g/cc and the collagen has a density of about 0.02 g/cc to about 1.0 g/cc of the putty and the putty comprises from about 60% to about 90% by volume of a liquid or about 60% to about 90% liquid volume percentage.

In some embodiments, the implantable osteoconductive matrix is a putty comprising ceramic and collagen and the ceramic has a density of about 0.10 g/cc and the collagen has a density of about 0.02 g/cc of the putty before the putty is hydrated with a liquid. Thus, in this embodiment, the putty is in its dry weight form.

In some embodiments, the implantable osteoconductive matrix is a putty comprising ceramic and collagen and the ceramic has a density of about 0.29 g/cc and the collagen has a density of about 0.06 g/cc of the putty and the putty comprises a liquid that occupies from about 80% to about 85% by volume of the final volume of the putty after the putty is hydrated with a liquid.

One suitable putty for use in the present application is MasterGraft® Putty produced by Medtronic Sofamor Danek, Inc.

Medical putties of the present application also include an amount of a particulate mineral material. In certain embodiments, the particulate mineral is incorporated in the putty at a level of at least about 0.25 g/cc of putty, typically in the range of about 0.25 g/cc to about 0.35 g/cc. Such relatively high levels of mineral will be helpful in providing a scaffold for the ingrowth of new bone.

In some embodiment, the putty comprises a natural or synthetic mineral that is effective to provide a scaffold for bone ingrowth. Illustratively, the mineral may be selected from one or more materials from the group consisting of bone particles, Bioglass, tricalcium phosphate, biphasic calcium phosphate, hydroxyapatite, corraline hydroxyapatite, and biocompatible ceramics. Biphasic calcium phosphate is a particularly desirable synthetic ceramic for use in the present application. Such biphasic calcium phosphate can have a tricalcium phosphate: hydroxyapatite weight ratio of about 50:50 to about 95:5, more preferably about 70:30 to about 95:5, even more preferably about 80:20 to about 90:10, and most preferably about 85:15. The mineral material can be particulate having an average particle diameter between about 0.4 and 5.0 mm, more typically between about 0.4 and 3.0 mm, and desirably between about 0.4 and 2.0 mm.

A putty of the present application can include a significant proportion of a liquid carrier, which will generally be an aqueous liquid such as water, saline, dextrose, buffered solutions or the like. In one aspect, a malleable, cohesive, shape-retaining putty of the present application comprises about 60% to 75% by weight of an aqueous liquid medium, such as water, advantageously about 65% to 75% by weight of an aqueous liquid medium (e.g. water) and a statin.

A putty of the present application includes a statin wherein the statin is in the putty from 0.1 mg/cc to 100 mg/cc. In some embodiments, the putty releases 40 ng to about 5 mg of the statin every hour.

In some embodiments, the matrix releases at stating at a dose of about 1 mg to about 100 mg/day (e.g., 1.6 mg to 3.2 mg/day) for up to 28 days for bone growth. In some embodiments, the load of statin in the matrix is from about 20 mg to 500 mg, for example 90 mg to 450 mg.

In use, the putty implant compositions are implanted at a site at which bone growth is desired, e.g. to treat a disease, defect or location of trauma, and/or to promote artificial arthrodesis. The putty enables their positioning, shaping and/or molding within voids, defects or other areas in which new bone growth is desired. In particularly advantageous embodiments, the shape-retaining property of the putty will desirably provide sufficient three-dimensional integrity to resist substantial compression when impinged by adjacent soft tissues of the body at a bony implant site.

Once in place, the osteoconductive putty can effectively induce and support the ingrowth of bone into the desired area even in a primate subject such as a human exhibiting a relatively slow rate of bone formation.

Osteoconductive putty compositions are especially advantageous when used in bones or bone portions that are vascularized to only moderate or low levels. These areas present particularly low rates of bone formation, and as such the rapid resorption of the carrier possess enhanced difficulties. Examples of moderate or only slightly vascularized sites include, for example, transverse processes or other posterior elements of the spine, the diaphysis of long bones, in particular the mid diaphysis of the tibia, and cranial defects.

In addition, in accordance with other aspects of the present application, the putty compositions can be incorporated in, on or around a load-bearing spinal implant device (e.g. having a compressive strength of at least about 10000 N) such as a fusion cage, dowel, or other device having a pocket, chamber or other cavity for containing an osteoconductive matrix, and used in a spinal fusion such as an interbody fusion.

Mineral Particles

In some embodiments, the matrix may comprise mineral particles that offers compression resistance. In some embodiments, the particles comprise at least 10%, 15%, 20%, 25%, 30%, 35%, 40%, 45%, 50%, 55%, 60%, 65%, 70%, 75%, 80%, 85%, 90%, 95% by weight of the matrix. In some embodiments, the particles are predominantly any shape (e.g., round, spherical, elongated (powders, chips, fibers, cylinders, etc.).

In some embodiments, the porosity of the particles comprises from 0 to 50%, in some embodiments, the porosity of the particles comprises 5% to 25%. In some embodiments, the particles are not entangled with each other but contact each other and portions of each particle overlap in the matrix to provide compression resistance. In some embodiments, at least 50%, 55%, 60%, 65%, 70%, 75%, 80%, 85%, 90%, 95%, or more of the particles overlap each other in the matrix.

In some embodiments, the particles are randomly distributed throughout the matrix. In other embodiments, the particles are uniformly or evenly distributed throughout the matrix. In some embodiments, the particles may be dispersed in the matrix using a dispersing agent. In other embodiments, the particles may be stirred in the polymer and the mechanical agitation will distribute the particles in the matrix until the desired distribution is reached (e.g., random or uniform).

In some embodiments, the matrix may comprise a resorbable ceramic (e.g., hydroxyapatite, tricalcium phosphate, bioglasses, calcium sulfate, etc.) tyrosine-derived polycarbonate poly (DTE-co-DT carbonate), in which the pendant group via the tyrosine—an amino acid—is either an ethyl ester (DTE) or free carboxylate (DT) or combinations thereof.

In some embodiments, the matrix may be seeded with harvested bone cells and/or bone tissue, such as for example, cortical bone, autogenous bone, allogenic bones and/or xenogenic bone. In some embodiments, the matrix may be seeded with harvested cartilage cells and/or cartilage tissue (e.g., autogenous, allogenic, and/or xenogenic cartilage tissue). For example, before insertion into the target tissue site, the matrix can be wetted with the graft bone tissue/cells, usually with bone tissue/cells aspirated from the patient, at a ratio of about 3:1, 2:1, 1:1, 1:3 or 1:2 by volume. The bone tissue/cells are permitted to soak into the matrix provided, and the matrix may be kneaded by hand or machine, thereby obtaining a pliable and cohesive consistency that may subsequently be packed into the bone defect. In some embodiments, the matrix provides a malleable, non-water soluble carrier that permits accurate placement and retention at the implantation site. In some embodiments, the harvested bone and/or cartilage cells can be mixed with the statin and seeded in the interior of the matrix.

In some embodiments, the particles in the matrix comprise a resorbable ceramic, bone, synthetic degradable polymer, hyaluronic acid, chitosan or combinations thereof. In some embodiments, the particles comprise cortical, cancellous, and/or corticocancellous, allogenic, xenogenic or transgenic bone tissue. The bone component can be fully mineralized or partially or fully demineralized or combinations thereof. The bone component can consist of fully mineralized or partially or fully demineralized bone.

In some embodiments, the matrix may contain an inorganic material, such as an inorganic ceramic and/or bone substitute material. Exemplary inorganic materials or bone substitute materials include but are not limited to aragonite, dahlite, calcite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, alpha-tricalcium phosphate, dicalcium phosphate, β-tricalcium phosphate, tetracalcium phosphate, amorphous calcium phosphate, octacalcium phosphate, BIOGLASS™, fluoroapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium sodium, potassium, etc.), or combinations or derivatives thereof.

In some embodiments, by including inorganic ceramics, such as for example, calcium phosphate, in the matrix, this will act as a local source of calcium and phosphate to the cells attempting to deposit new bone. The inorganic ceramic also provides compression resistance and load bearing characteristics to the matrix.

In some embodiments, the mineral particles in the matrix comprise tricalcium phosphate and hydroxyapatite in a ratio of about 80:20 to about 90:10. In some embodiments, the mineral particles in the matrix comprise tricalcium phosphate and hydroxyapatite in a ratio of about 85:15.

In some embodiments, the matrix has a density of between about 1.6 g/cm$^3$, and about 0.05 g/cm$^3$. In some embodiments, the matrix has a density of between about 1.1 g/cm$^3$, and about 0.07 g/cm$^3$. For example, the density may be less than about 1 g/cm$^3$, less than about 0.7 g/cm$^3$, less than about 0.6 g/cm$^3$, less than about 0.5 g/cm$^3$, less than about 0.4 g/cm$^3$, less than about 0.3 g/cm$^3$, less than about 0.2 g/cm$^3$, or less than about 0.1 g/cm$^3$.

In some embodiments, the diameter or diagonal of the matrix can range from 1 mm to 50 mm. In some embodiments, the diameter or diagonal of the matrix can range from 1 mm to 30 mm, or 5 mm to 10 mm which is small enough to fit through an endoscopic cannula, but large enough to minimize the number of matrices needed to fill a large the bone defect (e.g., osteochondral defect). In some embodiments, at the time of surgery, the matrix can be soaked with a statin and molded by the surgeon to the desired shape to fit the tissue or bone defect.

FIG. 1 illustrates a magnified side sectional view of an embodiment of the implantable matrix 10 injected as a long strand shown with collagen fibers 16 embedded randomly throughout it. In this figure, the matrix is porous and will allow cell migration into or over the porous interior of the matrix to enhance bone and/or cartilage remodeling. The pores also allow the introduction of a statin 14 and for it to be retained throughout it. The statin has anabolic activity and stimulates bone morphogenic protein expression and bone growth into the matrix to heal bone. Although the matrix is shown as a long strand, it will be understood that matrix can take on any shape and be malleable, cohesive and can be injected at or near the target tissue site.

Figure 2:
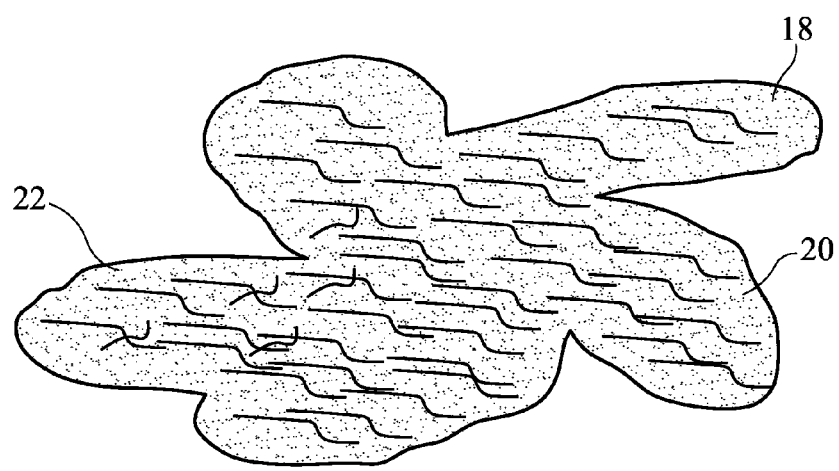
FIG. 2 illustrates a magnified side sectional view of an embodiment of the implantable matrix shown in an amorphous shape that can be moldable to conform to gaps or voids in the bone defect. The implantable matrix is shown with fibers embedded randomly throughout it.

FIG. 2 illustrates a magnified side sectional view of an embodiment of the implantable matrix 18 shown in an amorphous shape that can be moldable to conform to gaps or voids in the bone defect. The implantable matrix is shown with collagen fibers 22 embedded randomly throughout it. The implantable matrix is porous and also allows the introduction of a statin 20 and for it to be retained throughout it.

Figure 3:
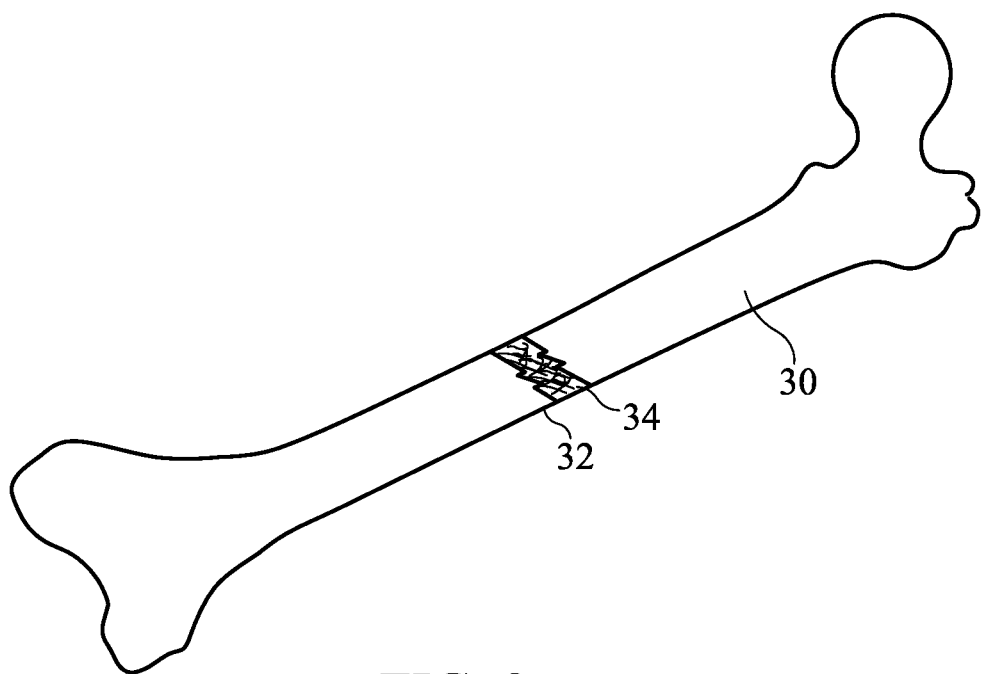
FIG. 3 illustrates a sectional view of a fractured femur and the fracture being filled with an embodiment of the implantable matrix.

FIG. 3 illustrates a sectional view of a fractured femur 30 and the fracture 32 being filled with an embodiment of the implantable matrix 34 that is moldable to conform to the fracture site. The matrix provides for sustained release of the statin. For example, the statin is released from the implantable matrix 34 over a period of 2 to 6 weeks and has anabolic activity and stimulates bone morphogenic protein expression and bone growth into the matrix to rejoin bone and repair the fracture. The statin also increases angiogenesis which enhances new bone formation.

Figure 4:
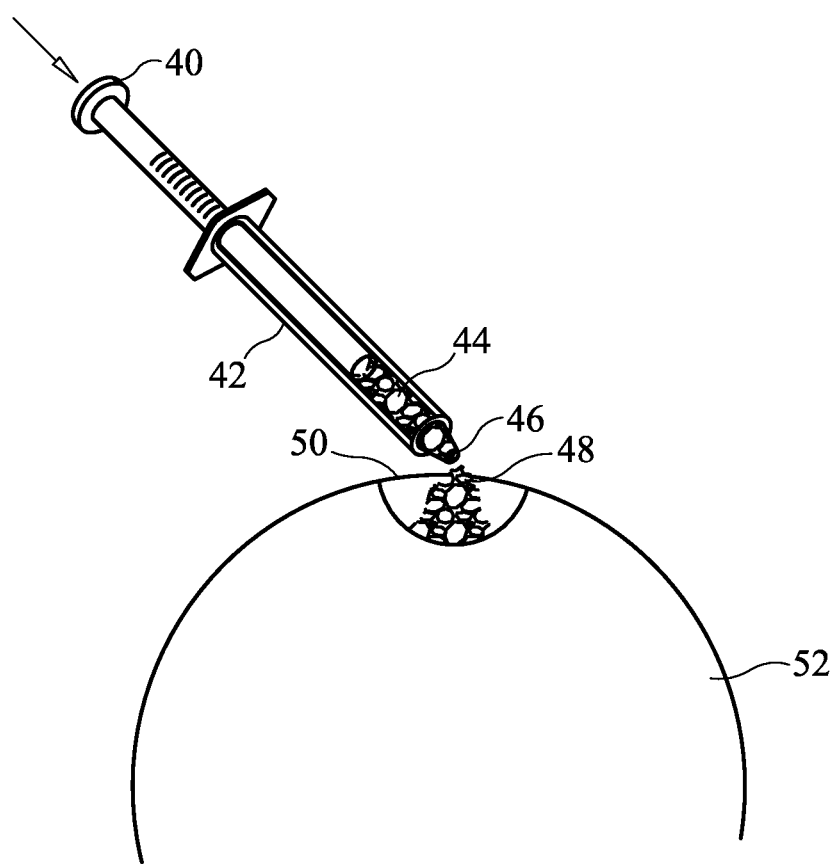
FIG. 4 illustrates a side partial cross-section view of an embodiment where a delivery system is applying the moldable, flowable, and cohesive matrix to a bone defect.

FIG. 4 illustrates a side partial cross-section view of an embodiment where a delivery system shown as a syringe 42 is applying the moldable, flowable, and cohesive matrix 44 to a bone defect 50 of a bone 52. The user pushes on plunger 40 causing the implantable matrix to flow 46 and be implanted 48 at the bone defect site 50.

Method of Making the Matrix

In some embodiments, the matrix may be made by injection molding, compression molding, blow molding, thermoforming, die pressing, slip casting, electrochemical machining, laser cutting, water-jet machining, electrophoretic deposition, powder injection molding, sand casting, shell mold casting, lost tissue scaffold casting, plaster-mold casting, ceramic-mold casting, investment casting, vacuum casting, permanent-mold casting, slush casting, pressure casting, die casting, centrifugal casting, squeeze casting, rolling, forging, swaging, extrusion, shearing, spinning, powder metallurgy compaction or combinations thereof.

One form of manufacturing the matrix involves casting the matrix material in a mold. The matrix material can take on the shape of the mold such as, crescent, quadrilateral, rectangular, cylindrical, plug, or any other shape. Additionally, the surface of the mold may be smooth or may include raised features or indentations to impart features to the matrix. Features from the mold can be imparted to the matrix as the matrix material in the mold is dried. In particular aspects, a roughened or friction engaging surface can be formed on the superior surface and/or the inferior surface of the matrix body. In some embodiments, protuberances or raised portions can be imparted on the superior surface and/or the inferior surface from the mold. Such examples of protuberances or raised portions are ridges, serrations, pyramids, and teeth, or the like.

In some embodiments, in manufacturing the matrix, a mixture of the matrix material (e.g., collagen) is combined with the mineral particles and a liquid to wet the material and form a slurry. Any suitable liquid can be used including, for example, aqueous preparations such as water, saline solution (e.g. physiological saline), sugar solutions, protic organic solvents, or liquid polyhydroxy compounds such as glycerol and glycerol esters, or mixtures thereof. The liquid may, for example, constitute about 5 to about 70 weight percent of the mixed composition prior to the molding operation. Certain liquids such as water can be removed in part or essentially completely from the formed matrix using conventional drying techniques such as air drying, heated drying, lyophilization, or the like.

In one embodiment of manufacture, a collagen mixture can be combined with mineral particles and a liquid, containing a statin and desirably with an aqueous preparation, to form a slurry. Excess liquid can be removed from the slurry by any suitable means, including for example by applying the slurry to a liquid-permeable mold or form and draining away excess liquid.

Before, during or after molding, including in some instances the application of compressive force to the collagen containing material, the collagen material can be subjected to one or more additional operations such as heating, lyophilizing and/or crosslinking to make the porous collagen interior or exterior of the matrix the desired porosity and to disperse the statin within the matrix. In this regard, crosslinking can be used to improve the strength of the formed matrix. Alternatively, one or more of the surfaces of the matrix can be crosslinked to reduce the size of the pores of the porous interior and thereby form the exterior of the matrix that is less permeable and/or less porous than the porous interior. Crosslinking can be achieved, for example, by chemical reaction, the application of energy such as radiant energy (e.g. UV light or microwave energy), drying and/or heating and dye-mediated photo-oxidation; dehydrothermal treatment; enzymatic treatment or others.

Chemical crosslinking agents will generally be preferred, including those that contain bifunctional or multifunctional reactive groups, and which react with matrix. Chemical crosslinking can be introduced by exposing the matrix material to a chemical crosslinking agent, either by contacting it with a solution of the chemical crosslinking agent or by exposure to the vapors of the chemical crosslinking agent. This contacting or exposure can occur before, during or after a molding operation. In any event, the resulting material can then be washed to remove substantially all remaining amounts of the chemical crosslinker if needed or desired for the performance or acceptability of the final implantable matrix.

Suitable chemical crosslinking agents include mono- and dialdehydes, including glutaraldehyde and formaldehyde; polyepoxy compounds such as glycerol polyglycidyl ethers, polyethylene glycol diglycidyl ethers and other polyepoxy and diepoxy glycidyl ethers; tanning agents including polyvalent metallic oxides such as titanium dioxide, chromium dioxide, aluminum dioxide, zirconium salt, as well as organic tannins and other phenolic oxides derived from plants; chemicals for esterification or carboxyl groups followed by reaction with hydrazide to form activated acyl azide functionalities in the collagen; dicyclohexyl carbodiimide and its derivatives as well as other heterobifunctional crosslinking agents; hexamethylene diisocyante; and/or sugars, including glucose, will also crosslink the matrix material.

In some embodiments, the matrices are formed by mixing the mineral particles in with a polymer slurry such as collagen and statin and pouring into a shaped mold. The composite mixture is freeze dried and possibly chemically crosslinked and cut to the final desired shape and then the matrix can be re-hydrated before use, where the surgeon can mold it to fit the bone defect.

In some embodiments, the matrix may comprise sterile and/or preservative free material. The matrix can be implanted by hand or machine in procedures such as for example, laparoscopic, arthroscopic, neuroendoscopic, endoscopic, rectoscopic procedures or the like.

The matrix of the present application may be used to repair bone and/or cartilage at a target tissue site, e.g., one resulting from injury, defect brought about during the course of surgery, infection, malignancy or developmental malformation. The matrix can be utilized in a wide variety of orthopedic, periodontal, neurosurgical, oral and maxillofacial surgical procedures such as the repair of simple and/or compound fractures and/or non-unions; external and/or internal fixations; joint reconstructions such as arthrodesis; general arthroplasty; cup arthroplasty of the hip; femoral and humeral head replacement; femoral head surface replacement and/or total joint replacement; repairs of the vertebral column including spinal fusion and internal fixation; tumor surgery, e.g., deficit filling; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay implantable matrices; implant placement and revision; sinus lifts; cosmetic procedures; etc. Specific bones which can be repaired or replaced with the implantable matrix herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal and/or metatarsal bones.

Statins

The matrix comprises a statin that can be disposed within, on throughout or in certain regions of the matrix. In some embodiments, the interior of the matrix is loaded with a statin that functions as a nidus or nest for new bone to deposit and grow.

Statins include one or more compound(s) sharing the capacity to competitively inhibit the hepatic enzyme 3-hydroxy-3-methylglutaryl coenzyme A (HMG-CoA) reductase. Compounds that inhibit the activity of HMG CoA reductase can be readily identified by using assays well known in the art; see, as examples, the assays described or cited in U.S. Pat. No. 4,231,938 at column 6, and in International Patent Publication WO 84/02131 at pp. 30-33.

Examples of a useful statin that can be in, on or throughout the matrix include, but is not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Appln. Publ. No. 738510 A2, the entire disclosure is herein incorporated by reference), eptastatin, pitavastatin, or pharmaceutically acceptable salts thereof or a combination thereof. In various embodiments, the statin may comprise mixtures of (+)R and (-)-S enantiomers of the statin. In various embodiments, the statin may comprise a 1:1 racemic mixture of the statin.

In various embodiments, natural products such as, for example, red yeast rice; Zhitai, Cholestin or Hypocol, and Xuezhikang contain statin compounds that act as HMG CoA reductase inhibitors.

Lovastatin is a statin that may be obtained from various manufacturers in various forms (e.g., injection, powder, etc.). For example, lovastatin may be obtained from Merck as Mevacor® (see U.S. Pat. No. 4,231,938, the entire disclosure is herein incorporated by reference). Suitable pharmaceutically acceptable salts of lovastatin include one or more compounds derived from bases such as sodium hydroxide, potassium hydroxide, lithium hydroxide, calcium hydroxide, 1-deoxy-2-(methylamino)-D-glucitol, magnesium hydroxide, zinc hydroxide, aluminum hydroxide, ferrous or ferric hydroxide, ammonium hydroxide or organic amines such as N-methylglucamine, choline, arginine or the like or combinations thereof. Suitable pharmaceutically acceptable salts of atorvastin include lithium, calcium, hemicalcium, sodium, potassium, magnesium, aluminum, ferrous or ferric salts thereof or a combination thereof.

In various embodiments, the therapeutically effective amount of lovastatin that can be placed in the matrix comprises from about 0.1 mg to about 2000 mg, for example, 0.1 mg to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, or 100 mg of lovastatin per day. In various embodiments, dosages of from 10 to 500 mg per day may be given, which for a normal human adult of approximately 70 kg is a dosage of from 0.14 to 7.1 mg/kg of body weight per day. In various embodiments, the dosage may be, for example from 0.1 to 1.0 mg/kg per day or from about 0.3 mg/kg/day to 3 mg/kg/day or from 40 ng/hr or 0.4 mcg/hr or from 6.9 mcg/kg/day to 0.68 mg/kg/day.

Atorvastatin is a statin that may be obtained from various manufacturers in various forms (e.g., injection, powder, etc.).

For example, atorvastatin may be obtained from Pfizer as Lipitor® (see U.S. Pat. No. 5,273,995, the entire disclosure is herein incorporated by reference). The pharmaceutically acceptable salts of atorvastatin include one or more compounds that generally can be derived by dissolving the free acid or the lactone; for example, the lactone, in aqueous or aqueous alcohol solvent or other suitable solvents with an appropriate base and isolating the salt by evaporating the solution or by reacting the free acid or lactone.

Suitable pharmaceutically acceptable salts of atorvastatin include one or more compounds derived from bases, such as for example, sodium hydroxide, potassium hydroxide, lithium hydroxide, calcium hydroxide, 1-deoxy-2-(methylamino)-D-glucitol, magnesium hydroxide, zinc hydroxide, aluminum hydroxide, ferrous or ferric hydroxide, ammonium hydroxide or organic amines such as N-methylglucamine, choline, arginine or the like or combinations thereof. Suitable pharmaceutically acceptable salts of atorvastin include lithium, calcium, hemicalcium, magnesium, zinc, sodium, potassium, magnesium, aluminum, ferrous or ferric salts thereof or a combination thereof.

In various embodiments, the therapeutically effective amount of atorvastatin that can be placed in the matrix comprises from about 0.1 mg to about 2000 mg, for example, 0.1 mg to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, or 100 mg of atorvastatin per day. In various embodiments, dosages of from 10 to 500 mg per day may be given, which for a normal human adult of approximately 70 kg is a dosage of from 0.14 to 7.1 mg/kg of body weight per day. In various embodiments, the dosage may be, for example from 0.1 to 1.0 mg/kg per day or from about 0.3 mg/kg/day to 3 mg/kg/day.

Simvastatin is a statin that may be obtained from various manufacturers in various forms (e.g., injection, powder, etc.). For example, simvastatin may be obtained from Merck as Zocor® (see U.S. Pat. No. 4,444,784, the entire disclosure is herein incorporated by reference). The pharmaceutically acceptable salts of simvastatin include those formed from cations such as, for example, sodium, potassium, aluminum, calcium, lithium, magnesium, zinc or tetramethylammonium as well as those salts formed from amines such as, for example, ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-ylmethylbenz-imidazole, diethylamine, piperazine, or tris(hydroxymethyl)aminomethane or a combination thereof.

In various embodiments, the therapeutically effective amount of simvastatin in the matrix comprises from about 0.1 mg to about 2000 mg, for example, 0.1 mg to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, or 100 mg of simvastatin per day. In various embodiments, dosages of from 10 to 500 mg per day may be given, which for a normal human adult of approximately 70 kg is a dosage of from 0.14 to 7.1 mg/kg of body weight per day. In various embodiments, the dosage may be, for example from 0.1 to 1.0 mg/kg per day or from about 0.3 mg/kg/day to 3 mg/kg/day.

In various embodiments, the therapeutically effective amount of mevastatin in the matrix comprises from about 0.1 mg to about 2000 mg, for example, 0.1 mg to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, or 100 mg of mevastatin per day. In various embodiments, dosages of from 10 to 500 mg per day may be given, which for a normal human adult of approximately 70 kg is a dosage of from 0.14 to 7.1 mg/kg of body weight per day. In various embodiments, the dosage may be, for example from 0.1 to 1.0 mg/kg per day or from about 0.3 mg/kg/day to 3 mg/kg/day.

Pravastatin is a statin that may be obtained from various manufacturers in various forms (e.g., injection, powder, liquid, etc.). For example, pravastatin may be obtained from Bristol-Myers Squibb as Pravachol® (see U.S. Pat. No. 4,346,227, the entire disclosure is herein incorporated by reference). Suitable pharmaceutically acceptable salts of pravastatin include one or more compounds derived from bases or acids, such as for example, sodium hydroxide, potassium hydroxide, lithium hydroxide, calcium hydroxide, 1-deoxy-2-(methylamino)-D-glucitol, magnesium hydroxide, zinc hydroxide, aluminum hydroxide, ferrous or ferric hydroxide, ammonium hydroxide, hydroxy-carboxylic acids or organic amines such as N-methylglucamine, choline, arginine or the like or esters of the hydroxy-carboxylic acids of pravastatin or a combination thereof. Suitable pharmaceutically acceptable salts of pravastatin include lithium, calcium, hemicalcium, magnesium, zinc, sodium, potassium, magnesium, aluminum, ferrous or ferric salts thereof a combination thereof.

In various embodiments, the therapeutically effective amount of pravastatin in the matrix comprises from about 0.1 mg to about 2000 mg, for example, 0.1 mg to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, or 100 mg of pravastatin per day. In various embodiments, dosages of from 10 to 500 mg per day may be given, which for a normal human adult of approximately 70 kg is a dosage of from 0.14 to 7.1 mg/kg of body weight per day. In various embodiments, the dosage may be, for example from 0.1 to 1.0 mg/kg per day or from about 0.3 mg/kg/day to 3 mg/kg/day.

Cerivastatin (also known as rivastatin) is a statin that may be obtained from various manufacturers in various forms (e.g., injection, powder, liquid, etc.). For example, cerivastatin may be obtained from Bayer AG as Baychol® (see U.S. Pat. No. 5,502,199, the entire disclosure is herein incorporated by reference). Suitable pharmaceutically acceptable salts of cerivastatin include one or more compounds derived from bases, such as for example, sodium hydroxide, potassium hydroxide, lithium hydroxide, calcium hydroxide, 1-deoxy-2-(methylamino)-D-glucitol, magnesium hydroxide, zinc hydroxide, aluminum hydroxide, ferrous or ferric hydroxide, ammonium hydroxide or organic amines such as N-methylglucamine, choline, arginine or the like or combinations thereof. Suitable pharmaceutically acceptable salts of cerivastatin include lithium, calcium, hemicalcium, magnesium, zinc, sodium, potassium, magnesium, aluminum, ferrous or ferric salts thereof or a combination thereof.

In various embodiments, the therapeutically effective amount of cerivastatin in the matrix comprises from about 0.1 mg to about 2000 mg, for example, 0.1 mg to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, or 100 mg of cerivastatin per day. In various embodiments, dosages of from 10 to 500 mg per day may be given, which for a normal human adult of approximately 70 kg is a dosage of from 0.14 to 7.1 mg/kg of body weight per day. In various embodiments, the dosage may be, for example from 0.1 to 1.0 mg/kg per day or from about 0.3 mg/kg/day to 3 mg/kg/day.

Fluvastatin is a statin that may be obtained from various manufacturers in various forms (e.g., injection, powder, liquid, etc.). For example, fluvastatin may be obtained from Novartis Pharmaceuticals as Lescol® (see U.S. Pat. No. 5,354,772, the entire disclosure is herein incorporated by reference). Some examples, of pharmaceutically acceptable salts include, for example, pharmaceutically acceptable salts of phosphoric acid such as tribasic calcium phosphate or inorganic carbonate and bicarbonate salts, e.g., sodium carbonate, sodium bicarbonate, calcium carbonate, or mixtures thereof. Suitable pharmaceutically acceptable salts of fluvastatin include lithium, calcium, hemicalcium, magnesium, zinc, sodium, potassium, magnesium, aluminum, ferrous or ferric salts thereof or a combination thereof.

In various embodiments, the therapeutically effective amount of fluvastatin comprises from about 0.1 mg to about 2000 mg, for example, 0.1 mg to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, or 100 mg of fluvastatin per day. For example, the dose may be 0.1 to 10 mg/kg of body weight.

Rosuvastatin is a statin that may be obtained from various manufacturers in various forms (e.g., injection, powder, liquid, etc.). For example, rosuvastatin may be obtained from AstraZeneca as Crestor® (See U.S. Pat. Nos. 6,316,460, 6,858,618, and RE37314, the entire disclosures are herein incorporated by reference). Suitable pharmaceutically acceptable salts of rosuvastatin include one or more compounds derived from bases, such as for example, sodium hydroxide, potassium hydroxide, lithium hydroxide, calcium hydroxide, 1-deoxy-2-(methylamino)-D-glucitol, magnesium hydroxide, zinc hydroxide, aluminum hydroxide, ferrous or ferric hydroxide, ammonium hydroxide or organic amines such as N-methylglucamine, choline, arginine or the like or combinations thereof. Suitable pharmaceutically acceptable salts of rosuvastatin include lithium, calcium, hemicalcium, tribasic calcium phosphate, magnesium, zinc, sodium, potassium, magnesium, aluminum, ferrous or ferric salts thereof or a combination thereof.

In various embodiments, the therapeutically effective amount of rosuvastatin comprises from about 0.1 mg to about 2000 mg, for example, 0.1 mg to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, or 100 mg of rosuvastatin per day. In various embodiments, dosages of from 10 to 500 mg per day may be given, which for a normal human adult of approximately 70 kg is a dosage of from 0.14 to 7.1 mg/kg of body weight per day. In various embodiments, the dosage may be, for example from 0.1 to 1.0 mg/kg per day or from about 0.3 mg/kg/day to 3 mg/kg/day.

Pitavastatin is a statin that may be obtained from various manufacturers in various forms (e.g., injection, powder, liquid, etc.). Suitable pharmaceutically acceptable salts of pitavastatin include one or more compounds derived from bases, such as for example, sodium hydroxide, potassium hydroxide, lithium hydroxide, calcium hydroxide, 1-deoxy-2-(methylamino)-D-glucitol, magnesium hydroxide, zinc hydroxide, aluminum hydroxide, ferrous or ferric hydroxide, ammonium hydroxide or organic amines such as N-methylglucamine, choline, arginine or the like or combinations thereof. Suitable pharmaceutically acceptable salts of pitavastatin include lithium, calcium, hemicalcium, tribasic calcium phosphate, magnesium, zinc, sodium, potassium, magnesium, aluminum, ferrous or ferric salts thereof or a combination thereof.

In various embodiments, the dosage of pitavastatin can be between 1 to 100 mg/day for example 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, or 100 mg of pitavastatin. In various embodiments, pitavastatin may be given at a dose of, for example, from 0.1 to 1.0 mg/kg per day or from about 0.3 mg/kg/day to 3 mg/kg/day.

Eptastatin, velostatin, fluindostatin, or dalvastain are statins that may be obtained from various manufacturers in various forms (e.g., injection, powder, liquid, etc.). Suitable pharmaceutically acceptable salts of eptastatin, velostatin, fluindostatin, or dalvastain include one or more compounds derived from bases, such as for example, sodium hydroxide, potassium hydroxide, lithium hydroxide, calcium hydroxide, 1-deoxy-2-(methylamino)-D-glucitol, magnesium hydroxide, zinc hydroxide, aluminum hydroxide, ferrous or ferric hydroxide, ammonium hydroxide or organic amines such as N-methylglucamine, choline, arginine or the like or combinations thereof. Suitable pharmaceutically acceptable salts of eptastatin, velostatin, fluindostatin, or dalvastain include lithium, calcium, hemicalcium, tribasic calcium phosphate, magnesium, zinc, sodium, potassium, magnesium, aluminum, ferrous or ferric salts thereof or a combination thereof.

In various embodiments, the dosage of eptastatin, velostatin, fluindostatin, or dalvastain can be between 1 to 100 mg/day for example 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, or 100 mg of eptastatin velostatin, fluindostatin, or dalvastain. In various embodiments, eptastatin may be given at a dose of, for example, from 0.1 to 1.0 mg/kg per day or from about 0.3 mg/kg/day to 3 mg/kg/day.

The statin may be incorporated directly into the matrix. Alternatively, the statin may be incorporated into polymeric or non-polymeric material, as well as synthetic or naturally occurring material (as discussed above) and formed into capsules, microspheres, microparticles, microcapsules, microfibers particles, nanospheres, nanoparticles, coating, matrices, wafers, pills, pellets, emulsions, liposomes, micelles, gels, or other pharmaceutical delivery compositions and then applied in or to the matrix. Suitable materials for incorporating the statin are pharmaceutically acceptable biodegradable and/or any bioabsorbable materials that are preferably FDA approved or GRAS materials.

In some embodiments, a statin and/or other therapeutic agent may be disposed on or in the matrix by hand, electrospraying, ionization spraying or impregnating, vibratory dispersion (including sonication), nozzle spraying, compressed-air-assisted spraying, injecting, brushing and/or pouring. For example, a statin such as lovastatin may be disposed on or in the biodegradable matrix by the surgeon before the biodegradable matrix is administered or the matrix may be pre-loaded with the statin by the manufacturer beforehand.

The statin may contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfite, sodium thiosulfate, thimerosal, methylparaben, polyvinyl alcohol and phenylethyl alcohol; solubility adjusting agents; stabilizers; and/or cohesion modifiers. In some embodiments, the statin may comprise sterile and/or preservative free material.

These above inactive ingredients may have multi-functional purposes including the carrying, stabilizing and controlling the release of the statin and/or other therapeutic agent(s). The sustained release process, for example, may be by a solution-diffusion mechanism or it may be governed by an erosion-sustained process.

In some embodiments, a pharmaceutically acceptable formulation comprising a statin is provided, wherein the formulation is a freeze-dried or lyophilized formulation containing the matrix. Typically, in the freeze-dried or lyophilized formulation an effective amount of a statin is provided. Lyophilized formulations can be reconstituted into solutions, suspensions, emulsions, or any other suitable form for administration or use. The lyophilized formulation may comprise the liquid used to reconstitute the statin. Lyophilized formulations are typically first prepared as liquids, then frozen and lyophilized. The total liquid volume before lyophilization can be less, equal to, or more than the final reconstituted volume of the lyophilized formulation. The lyophilization process is well known to those of ordinary skill in the art, and typically includes sublimation of water from a frozen formulation under controlled conditions.

Lyophilized formulations can be stored at a wide range of temperatures. Lyophilized formulations may be stored at or below 30° C., for example, refrigerated at 4° C., or at room temperature (e.g., approximately 25° C.).

Lyophilized formulations of the statin are typically reconstituted for use by addition of an aqueous solution to dissolve the lyophilized formulation. A wide variety of aqueous solutions can be used to reconstitute a lyophilized formulation. In some embodiments, lyophilized formulations can be reconstituted with a solution containing water (e.g., USP WFI, or water for injection) or bacteriostatic water (e.g., USP WFI with 0.9% benzyl alcohol). However, solutions comprising buffers and/or excipients and/or one or more pharmaceutically acceptable carries can also be used. In some embodiments, the solutions do not contain any preservatives (e.g., are preservative free).

Application of the Statin to the Matrix

In some embodiments, a therapeutic agent (including one or more statins) may be disposed on or in the interior of the matrix by hand, electrospraying, ionization spraying or impregnating, vibratory dispersion (including sonication), nozzle spraying, compressed-air-assisted spraying, injecting, brushing and/or pouring.

Application of the statin to the matrix may occur at the time of surgery or by the manufacturer or in any other suitable manner. For example, the statin may be further reconstituted using a syringe and the syringe can be placed into the interior of the matrix via insertion of a needle or cannula (piercing the matrix) and placing it into the interior of the matrix and injecting the statin so it is evenly distributed throughout the porous interior.

In some embodiments, the statin may be applied to the matrix (i.e., collagen) prior to combining the materials and forming it into the final matrix shape. Indeed, the statin can be blended into the natural or synthetic polymer (i.e., POE) and poured into molds of the final shape of the matrix. Alternatively, the statin, such as lovastatin, can be incorporated in a suitable liquid carrier, and applied onto and/or into the porous loaded matrix after forming it into the final shape by soaking, dripping, injecting, spraying, etc. or the matrix can be molded into the desired shape.

In some embodiments, the lyophilized statin can be disposed in a vial by the manufacturer and then the surgeon can mix the diluent with the lyophilized statin. The matrix then can be parenterally administered to the target tissue site. The term "parenteral" as used herein refers to modes of administration which bypass the gastrointestinal tract, and include for example, intramuscular, intraperitoneal, intrasternal, subcutaneous, intra-operatively, intravenously, intrathecally, intradiscally, peridiscally, epidurally, perispinally, intraarticular or combinations thereof.

In some embodiments, the statin is supplied in a liquid carrier (e.g., an aqueous buffered solution). Exemplary aqueous buffered solutions include, but are not limited to, TE, HEPES (2-[4-(2-hydroxyethyl)-1-piperazinyl]ethanesulfonic acid), MES (2-morpholinoethanesulfonic acid), sodium acetate buffer, sodium citrate buffer, sodium phosphate buffer, a Tris buffer (e.g., Tris-HCL), phosphate buffered saline (PBS), sodium phosphate, potassium phosphate, sodium chloride, potassium chloride, glycerol, calcium chloride or a combination thereof. In various embodiments, the buffer concentration can be from about 1 mM to 100 mM.

Additional Therapeutic Agents

The statins of the present application may be disposed on or in the matrix with other therapeutic agents. For example, the statin may be disposed on or in the carrier by electro spraying, ionization spraying or impregnating, vibratory dispersion (including sonication), nozzle spraying, compressed-air-assisted spraying, brushing and/or pouring.

Exemplary therapeutic agents include but are not limited to IL-1 inhibitors, such Kineret® (anakinra), which is a recombinant, non-glycosylated form of the human interleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as antioxidants, such as dithiocarbamate, and other compounds, such as, for example, sulfasalazine.

Examples of therapeutic agents suitable for use also include, but are not limited to, an anti-inflammatory agent, analgesic agent, or osteoinductive growth factor or a combination thereof. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine[2-hydroxy-5-[4-[C2-pyridinylamino)sulfonyl]azo]benzoic acid, sulindac, tepoxalin, and tolmetin; as well as antioxidants, such as dithiocarbamate, steroids, such as cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable analgesic agents include, but are not limited to, acetaminophen, bupivicaine, fluocinolone, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papavereturn, pentazocine, pethidine, phenoperidine, piritramide, dextropropoxyphene, remifentanil, tilidine, tramadol, codeine, dihydrocodeine, meptazinol, dezocine, eptazocine, flupirtine, amitriptyline, carbamazepine, gabapentin, pregabalin, or a combination thereof.

Kits

The matrix, statin and devices to administer the implantable matrix composition may be sterilizable. In various embodiments, one or more components of the matrix, and/or medical device to administer it may be sterilizable by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In some embodiments, the implantable matrix may be packaged in a moisture resistant package and then terminally sterilized by gamma irradiation. In use the surgeon removes the one or all components from the sterile package for use.

In various embodiments, electron beam (e-beam) radiation may be used to sterilize one or more components of the matrix. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize the implantable matrix and/or one or more components of the matrix, including, but not limited to, gas sterilization, such as, for example, with ethylene oxide or steam sterilization.

In various embodiments, a kit is provided comprising the statin, matrix, and/or diluents. The kit may include additional parts along with the implantable matrix combined together to be used to implant the matrix (e.g., wipes, needles, syringes, etc.). The kit may include the matrix in a first compartment. The second compartment may include a vial holding the statin, diluent and any other instruments needed for the localized drug delivery. A third compartment may include gloves, drapes, wound dressings and other procedural supplies for maintaining sterility of the implanting process, as well as an instruction booklet, which may include a chart that shows how to implant the matrix after reconstituting the statin. A fourth compartment may include additional needles and/or sutures. Each tool may be separately packaged in a plastic pouch that is radiation sterilized. A fifth compartment may include an agent for radiographic imaging. A cover of the kit may include illustrations of the implanting procedure and a clear plastic cover may be placed over the compartments to maintain sterility.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An implantable osteoconductive matrix configured to fit at or near a target tissue site, the matrix being malleable and cohesive and comprising a biodegradable polymer and a therapeutically effective amount of a statin disposed within the interior of the matrix, the matrix having a load of the statin between about 20 mg and 500 mg, wherein the matrix allows influx of at least progenitor, and/or bone cells therein, and the matrix comprises ceramic and collagen, the ceramic having a density of about 0.15 g/cc to about 0.45 g/cc of the matrix and the collagen having a density of about 0.02 g/cc to about 1.0 g/cc of the matrix and the matrix comprises mineral particles having a porosity of 5% to 25% dispersed therein having an average particle diameter in the range of 0.1 mm to 2 mm, and the mineral particles overlap each other by at least 75%, and the matrix comprises polyethylene glycol (PEG), magnesium, an antioxidant and trehalose, and wherein the matrix resist compression by at least 85% when force is applied to the matrix.

2. An implantable osteoconductive matrix according to claim 1, wherein: (i) the target tissue site is a bone fracture and the implantable osteoconductive matrix facilitates bone formation in the fracture or (ii) the implantable osteoconductive matrix is flowable and comprises an open porous network of natural or synthetic polymers and mineral particles or (iii) the implantable osteoconductive matrix is a putty comprising ceramic and collagen and the collagen has a density of about 0.02 g/cc of the putty before the putty is hydrated or (iv) the implantable osteoconductive matrix is a putty comprising ceramic and collagen and the ceramic has a density of about 0.29 g/cc and the collagen has a density of about 0.06 g/cc of the putty and the putty comprises a liquid that occupies from about 80% to about 85% by volume of the putty after the putty is hydrated.

3. An implantable osteoconductive matrix according to claim 1, wherein the implantable osteoconductive matrix is flowable and comprises a shape retaining putty comprising 50 wt % to 80 wt % of an aqueous liquid medium, and insoluble collagen fibers dispersed in the putty.

4. An implantable osteoconductive matrix according to claim 1, wherein: (i) the implantable osteoconductive matrix allows for cell infiltration, cell attachment, and acts as a nidus for osteoid deposition, and mineralized bone formation or (ii) the implantable osteoconductive matrix is a putty comprising ceramic and collagen and the putty comprises from about 60% to about 90% by volume of a liquid.

5. An implantable osteoconductive matrix according to claim 3, wherein the putty further comprises mineral particles that are at a level of 0.15 g/cc to 0.45 g/cc in the putty; and the insoluble collagen fibers in the putty are at a level of 0.04 g/cc to 0.1 g/cc of the putty.

6. An implantable osteoconductive matrix according to claim 1, wherein the statin comprises at least cerivastatin, atorvastatin, simvastatin, pravastatin, fluvastatin, lovastatin, rosuvastatin, eptastatin, pitavastatin, velostatin, fluindostatin, dalvastain, or pharmaceutically acceptable salts thereof or a combination thereof and the matrix is freeze dried and rehydrated at the time of use.

7. An implantable osteoconductive matrix according to claim 1, wherein the statin is in the matrix from 0.1 mg/cc to 100 mg/cc.

8. An implantable osteoconductive matrix according to claim 1, wherein the matrix releases 0.01 mg to about 5 mg of the statin every hour.

9. An implantable osteoconductive matrix according to claim 1, wherein (i) the matrix releases 50%, 60%, 70%, 80%, 90%, 95%, 99%, or 100% of the statin loaded in the matrix over a period of 3 to 6 weeks after the matrix is administered to the target tissue site; or (ii) the statin is encapsulated in microparticles, microspheres, microcapsules, and/or microfibers.

10. An implantable matrix according to claim 1, wherein the matrix comprises mineral particles that are resorbable and facilitate or accelerate new bone growth.

11. An implantable matrix according to claim 10, wherein the mineral particles comprise a cortical, cancellous, cortico-cancellous, allogenic, xenogenic or transgenic bone tissue, bone powder, demineralized bone powder, porous calcium phosphate ceramics, hydroxyapatite, tricalcium phosphate, bioactive glass or a combination thereof.

12. An implantable matrix according to claim 10, wherein (i) the mineral particles comprise tricalcium phosphate and hydroxyapatite in a ratio of about 70:30 to about 90:10 or (ii) the mineral particles comprise tricalcium phosphate and hydroxyapatite in a ratio of about 85:15; or (iii) the mineral particles represent at least 50 to 98 weight percent of the matrix.

13. An implantable matrix according to claim 1, wherein the matrix sets-up in situ.

14. An implantable osteoconductive matrix configured to fit at or near a target tissue site, the matrix being injectable, malleable and cohesive and comprising calcium phosphate having an average particle diameter in the range of 0.1 mm to 2 mm and a biodegradable polymer comprising collagen having a density of about 0.02 g/cc to about 1.0 g/cc of the matrix and a therapeutically effective amount of a statin disposed within the interior of the matrix, the matrix having a load of the statin between about 20 mg and 500 mg, wherein the matrix allows influx of at least progenitor, and/or bone cells therein, and the matrix comprises polyethylene glycol (PEG), magnesium, an antioxidant, hyaluronic acid, trehalose and mineral particles having a porosity of 5% to 25% that overlap each other by at least 75%, and wherein the matrix resist compression by at least 85% when force is applied to the matrix.

15. An implantable osteoconductive matrix according to claim 14, wherein the implantable osteoconductive matrix is deliverable via an injection and comprises a shape retaining putty comprising 50 wt % to 80 wt % of an aqueous liquid medium, insoluble collagen fibers and soluble collagen fibers dispersed in the putty.

16. An implantable osteoconductive matrix according to claim 15, wherein the calcium phosphate particles dispersed therein are at a level of 0.15 g/cc to 0.45 g/cc in the putty; and the insoluble collagen fibers in the putty are at a level of 0.04 g/cc to 0.1 g/cc of the putty.

17. An implantable osteoconductive matrix according to claim 1, wherein the matrix is stackable.

18. An implantable osteoconductive matrix according to claim 14, wherein the matrix comprises statin nanoparticles and is stackable.

* * * * *